United States Patent
Vitello

(10) Patent No.: US 6,585,691 B1
(45) Date of Patent: Jul. 1, 2003

(54) TAMPER EVIDENT END CAP ASSEMBLY FOR A LOADED SYRINGE AND PROCESS

(76) Inventor: Jonathan J. Vitello, 5035 NW. 98 Way, Coral Springs, FL (US) 33076

(*) Notice: Subject to any disclaimer, the term of this patent is extended or adjusted under 35 U.S.C. 154(b) by 0 days.

(21) Appl. No.: 09/853,261

(22) Filed: May 11, 2001

(51) Int. Cl.[7] ............................................... A61M 5/00
(52) U.S. Cl. ...................... 604/111; 604/187; 604/535; 220/DIG. 34; 215/230; 215/250
(58) Field of Search ................................ 604/162, 163, 604/164.08, 110, 111, 192, 199, 263, 533, 534, 535, 187, 200; 220/DIG. 34; 215/230, 250

(56) References Cited

U.S. PATENT DOCUMENTS

| 4,832,695 A | * | 5/1989 | Rosenberg et al. | ......... 604/111 |
| 5,328,474 A | * | 7/1994 | Raines | ....................... 215/213 |
| 6,126,640 A | * | 10/2000 | Tucker et al. | ................ 604/111 |
| 6,193,688 B1 | * | 2/2001 | Balestracci et al. | ......... 604/111 |
| 6,196,998 B1 | * | 3/2001 | Jansen et al. | ................ 604/111 |
| 6,394,983 B1 | * | 5/2002 | Mayoral et al. | ............. 604/192 |

* cited by examiner

Primary Examiner—Manuel Mendez
Assistant Examiner—Mark K. Han
(74) Attorney, Agent, or Firm—Malloy & Malloy, P.A.

(57) ABSTRACT

An improved tamper evident end cap assembly for a drug loaded syringe which assembly includes a syringe cap to close the discharge port in the nozzle of the syringe and an indicator ring about the nozzle connected by chads or tabs to a tubular shield which chads or tabs are adapted to break freeing the ring from the shield to loosely wobble on the nozzle indicating tampering if an axial force of separation is applied to the syringe cap to remove it from the syringe and a one way drive mechanism engaging both the shield and syringe cap so the shield may be rotated to advance the assembly onto a syringe nozzle but which is not responsive to counter rotation to withdraw the syringe cap to open the discharge port and gain access to the drug.

16 Claims, 4 Drawing Sheets

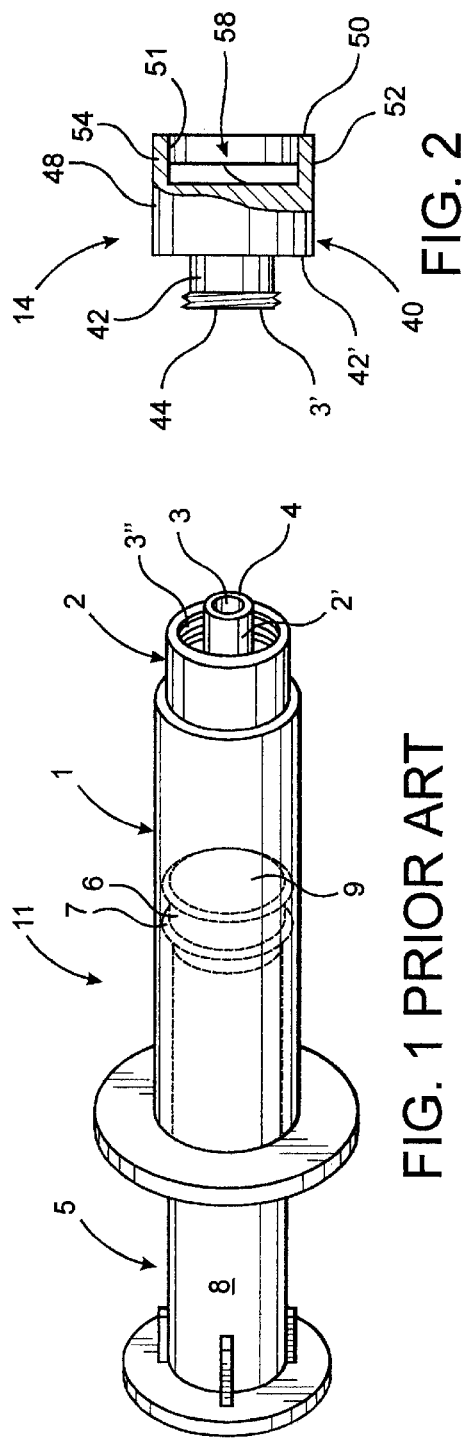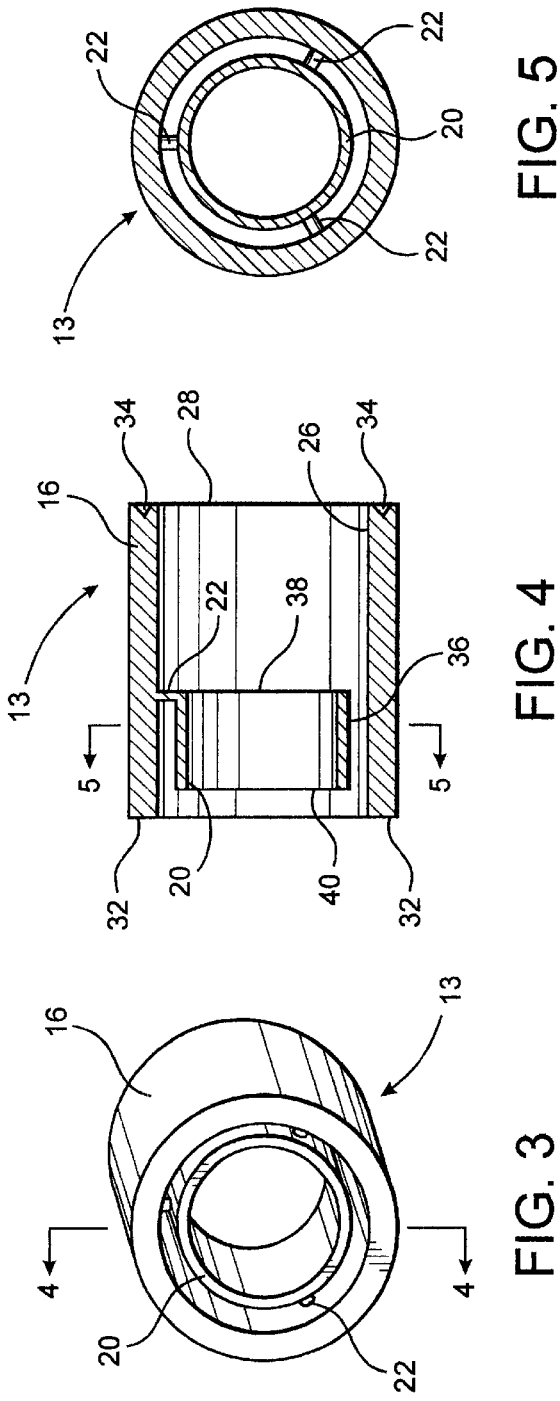

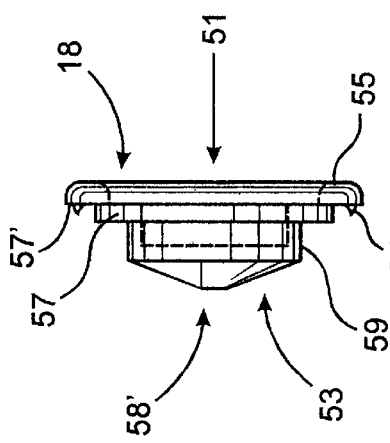
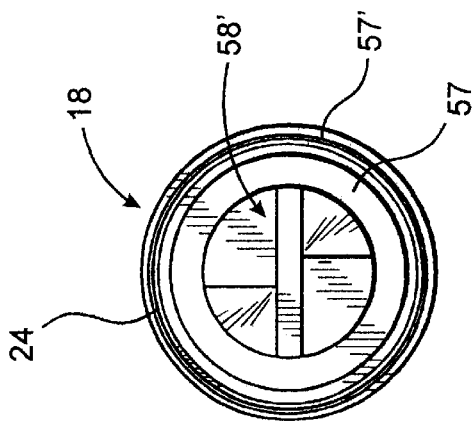
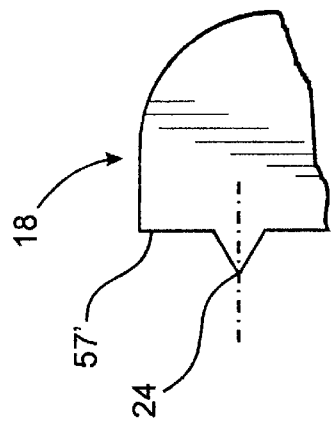
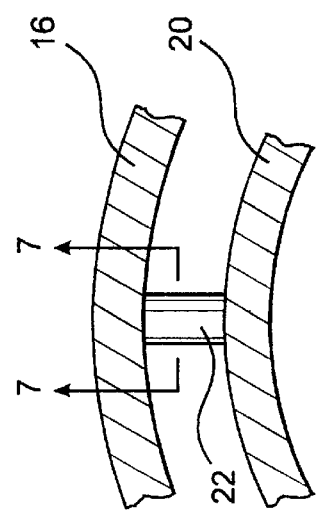
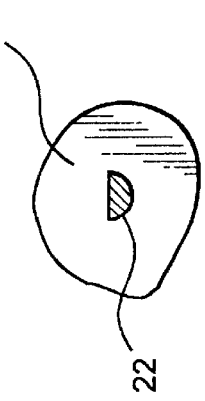

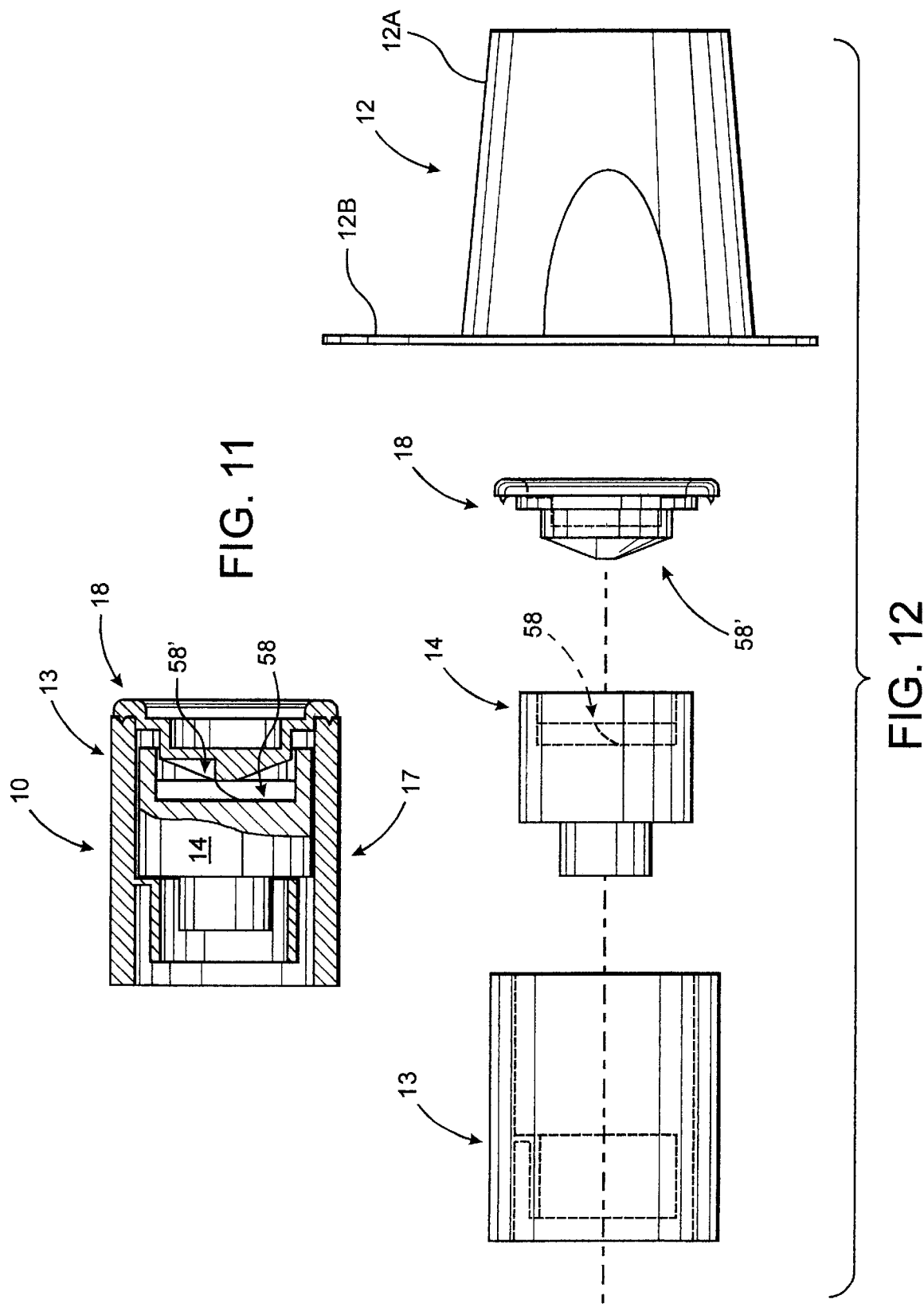

TAMPER EVIDENT END CAP ASSEMBLY FOR A LOADED SYRINGE AND PROCESS

BACKGROUND OF THE INVENTION

1. Field of the Invention

This invention relates to an improved tamper evident end cap assembly for a drug loaded syringe to seal it and to cap it protectively prior to injecting a patient with the drug; and, also, it relates to a package and the end cap assembly, as a combination, wherein the assembly is encapsulated within the package to be maintained in it in a sterile condition prior to capping a drug loaded syringe with it, and; further, it relates to a drug loaded syringe capped with the tamper evident end cap assembly ready to be opened to inject a patient with the drug or to return the drug load, if not used by the patient, to be down loaded at a station and recycled. The invention also relates to a process of manufacturing the end cap assembly and of using it by installing it on a mating syringe.

2. Description of the Related Art

This invention is disclosed in three forms:

a first form, which is a combination, composed of a drug loaded syringe having a nozzle with a discharge port or luer opening and a tamper evident end cap assembly according to the invention installed on the nozzle sealing and closing the luer opening and which cannot be removed to gain access to the drug load without creating palpable evidence of tampering;

a second form, which is another combination composed, of a) at least one tamper evident end cap assembly which has a structure according to the invention, and b) a sterile shipping and storage package encapsulating it, the end cap assembly including its end cap assembly luer lock syringe cap captivated within the end cap assembly is adapted to be removed from the package and installed on the nozzle of a mated standard syringe in a position from which it cannot be removed without creating evidence of the removal, and a third form which is an improved combination, composed of a) a tamper evident end cap assembly which includes b) a luer lock syringe cap coaxially captivated yet rotatable on its axis within the assembly, the assembly being for mounting of it over the discharge port or luer opening of a dose loaded standard and mated syringe, the end cap assembly being improved with respect to known devices by structure set forth fully in this disclosure which, among other elements, includes a) a first one way drive means component on the syringe cap, b) a floor portion in the assembly to maintain the cap within the assembly which floor portion also has a axial one way drive means component, which mates with the first component to comprise a one way drive means to move the syringe cap axially in one direction only to tighten it on a syringe nozzle, and is disengaged and inefficient upon rotation in the other direction of rotation and c) a centering means on the floor portion to guide the syringe cap of the end cap assembly into coaxial engaged relation with other end cap assembly parts.

The invention is also of a process of manufacture of the foregoing structure and of the use of it.

Throughout this specification, the phrase "standard syringe" is used. This phrase is intended to refer to a plurality of "carbon copy" syringes, usually made by a single manufacturer. A "carbon copy" syringe is one of a group of syringes of the same type, as regards size, shape and configuration which are intended to be used at a particular medical facility or location. By way of explanation, as is well known in the field, many facilities use standard syringes made and sold by a particular manufacturer, such as those of the Becton Dickenson Company; however, there are syringes of many other manufacturers which are also in use at many facilities; and these are also referred to herein as standard syringes. The point is that the subject invention is sized and shaped to mate with all of the "carbon copies" of a standard luer lock type syringe stocked for use at a given facility, regardless of the manufacture of the standard syringes used at that particular facility.

As further background generally, as indicated in FIG. 1, a standard luer lock type syringe 11 is usually of plastic material; and it typically includes a barrel 1 with a nozzle 2, which are usually transparent or translucent, and define an elongate interior chamber which is in fluid communication an axial luer, passageway or long channel 3 in the syringe nozzle 2 and that terminates distally at an opening or discharge port 4; and b) an axially slidable piston 5 in the barrel with a head 6 provided with a circumferential gasket means 7. When assembled, the end face 9 of the head 6 of the piston confronts channel 3 and closes the opening or discharge port 4 of the syringe. The piston, also, includes a push rod 8 extending proximally from the head 6 and from barrel 1 for axially manipulating the head end face 9 and, consequently, the axial location of the piston head 6 in the barrel 1, either closer to or withdrawn from, the luer opening or discharge port 4. In use, the standard syringe 11, after being loaded with a drug at the pharmacy, is sealed by closing the discharge port 4 with a mating member often referred to as a luer lock or syringe cap 14 as shown in FIG. 2. To do this the cap 14 may be provided with threads 3" to be threadably connected to the nozzle by a suitable mating connection means 3'. As shown in FIGS. 1 and 2, the threads 3" are located on the interior of the nozzle 2 so as to connect to an exterior of connection means 3'. The connection means of the luer lock or syringe cap 14 may, alternatively, be of the type which includes the male radially extending flange portion also indicated as 3' in FIG. 2. The connection may also be of the type which includes a set of circumferentially spaced ears (not shown) on the outer surface of the luer lock cap provided to threadably engage the threads on the syringe. As shown, generally, in FIG. 2 in either case, the ear type or the flange type, the radially extending portion 3' of the cap 14 is sized and configured for threaded receipt in the annular, correspondingly threaded recess 3" of the nozzle 2. In another form, the connection means may be merely reversed and comprise a female connection means portion on the luer lock or syringe cap for threaded connection with a male connection means portion on the nozzle 2. In some structures, the nozzle portion 2 and syringe cap 14 may each have a correspondingly tapered mating configuration for press fitting them together to join them. In this specification the term, "connection means" refers to and embraces the structure shown and or described as well as other known and usually routine means of installing a syringe cap 14 and a mated syringe 11 to close the discharge or dispensing port 4 of the syringe 11.

Turning now to the background purposes of the invention, in a hospital, for example, it is common for medical doctors to order that a patient be given an oral or an injectable dose of a drug. In the case of an injectable drug, the dose is quite often filled by a pharmacist at a location which may be regarded as a syringe filling station. It is often far from the place where the patient is to be injected. It is quite often that a syringe filling station is located on one floor of a hospital and the nurse's station is located on another hospital floor. Indeed, at large medical facilities, a syringe filling station may resemble a factory on the hospital grounds from which drug loaded syringes are delivered to multiple nurse stations in multiple other hospital buildings. Because of the remote location of many nurses stations relative to an associated syringe filling station, a loaded syringe is very often given to another person for delivery to a nurse station for subsequent dosing of the patient by a duly qualified nurse or other medically trained person.

During the process of loading the syringe with a drug dose, the delivery of the dosed syringe and its handling in general prior to the step of actually dosing a patient by injection, there is a danger of contamination. This invention guards against that happening.

Also, especially in the case of a very expensive drug or an addictive dose, there is a danger of tampering with the loaded syringe in an effort to improperly gain premature access to the drug. A real danger is that such inappropriate action may result in a substitution of an unauthorized material in the syringe, simulating an actual prescribed or real dose. Obviously, a substitution of a substitute dose for a real dose, such as a substitution of a saline solution for a dose of morphine, may have extremely serious consequences. Thus, there is a problem of knowing if a sealed drug laden syringe has, or has not, been exposed to contamination or compromised by tampering with it. This and other problems have been further described in my earlier granted U.S. Pat. No. 4,667,837 and in other patents including in U.S. Pat. No. 5,328,474.

This invention addresses problems of making and using drug loaded syringes, some of which are described in each of the above noted patents. This is because problems remain in the field since the introduction of products according to those two patents. These include problems of easy and inexpensive assembly of the end cap assemblies in the manufacture of them, problems involved in the assembly of an end cap assembly on a drug loaded syringe at a drug filling station, and problems of maintaining sterility during storage at the manufacturing facility of the end cap assemblies, transport of them to a medical or other facility storage, and problems of storage of them at a medical facility. In summary the invention addresses problems in handling the end cap assemblies as one is made and used at different stations by different persons. In general, this invention provides an improved tamper evident end cap assembly being less expensive, safe and structured for convenient manufacture and use.

Specifically, this invention addresses outstanding problems by providing: a) an improved tamper evident end cap assembly including a captivated luer lock syringe cap for closing the discharge port in the nozzle of a loaded syringe, b) an improved sterile package with the end cap assembly encapsulated within it, for transport to, and, prior to use, for storage at a medical facility; and c) an improved combination of a drug loaded syringe and tamper evident end cap assembly for use in dosing a patient. The end cap assembly is especially adapted to mate with and be used with what is referred to herein as a standard syringe, one which.is a "carbon copy" of the type used at a given medical facility where it is drug loaded and delivered to a nurse's station for injecting a patient with the dose. Any unauthorized access to the loaded drug contents, once the syringe has been loaded and closed prior to its ultimate use, requires removal of the syringe cap by an unauthorized person, and the fact that such a removal occurred is clearly evident, if it does in fact happen.

SUMMARY OF THE INVENTION

Generally, in a first form, this invention provides an improved tamper evident end cap assembly including a captivated luer lock syringe cap for closing the discharge port on the nozzle of a drug loaded syringe. In another form, the invention provides a combination composed of a) the improved end cap assembly and b) a sterile package to keep the end cap, or a plurality of such end cap assemblies, sterile during a period of storage at a manufacturing site, during transport of it to a medical facility, and during storage there until ready for use capping a drug loaded syringe. In yet another form, the invention is of an improved tamper evident end cap assembly mounted on a drug loaded syringe for the "last mile" delivery to a nurses's station ready for use by dosing a patient by injection.

One specific persistent and troubling problem that has remained in the field is overcome by the disclosed structure. That problem is caused by the fact that many syringes and doses are of very low volume. With earlier tamper evident syringes a problem has been that, inadvertently, a small loaded syringe can pass axially through an end cap assembly during the step of capping a drug loaded syringe. This is especially true in the case of syringes sized for a one cubic centimeter charge of a drug. The improved structure of this invention resolves this problem. It provides a blocking means so this cannot happen.

Another problem is that syringe drug doses are often wasted. In medical practice a doctor often writes orders directing that "up to" a certain amount of a drug, a limit which can be safely tolerated by a patient, may be administered, if requested by the patient or circumstances justify it. This often results in drug doses being loaded into many syringes which doses are not actually administrated. These drug doses can be routinely recycled provided if there is an assurance that the drug has not been contaminated and the syringe can be opened without comprising the drug. This invention provides structure which accommodates that purpose.

After being filled with a drug at a syringe filling station, the loaded syringe is delivered to an injection location for dosing a patient. Especially while being delivered, accidental contamination is substantially prevented by this invention; and, importantly, any unauthorized tampering in an effort to access a drug in a loaded syringe with an end cap assembly according to this invention is clearly evident. Also, whatever the specifications are of a manufacturer for his particular syringe, which is standard at a given facility, the invention is adapted to be "tailor made" or sized to accommodate that standard syringe of that facility.

OBJECTS OF THE INVENTION

It is an overall object of this invention to provide an improved tamper evident end cap assembly which includes a captivated lure lock syringe cap for closing the discharge port or, luer opening, in the nozzle of a loaded syringe.

It is also an object to provide a sterile combination composed of: a) one or more tamper evident end cap assemblies according to this invention which includes a mating luer lock syringe cap captivated in the assembly; and b) a sterile shipping and storage package encapsulating the assembly.

It is a further object to provide a captivated luer lock syringe cap which includes a) a first one way drive means component on the luer lock or syringe cap to mate with a companionate second one way drive means component on another part of the end cap assembly, which is a mirror image of the first component, and, when the components are engaged comprise a drive means to install the cap on a syringe, and, additionally, b) a means to center the lure lock syringe cap so that it is rotatable within the end cap assembly and also is in coaxial relation and engaged with the other end cap assembly parts for driving advancement of the end cap assembly in a single axial direction along a syringe nozzle upon relative rotation of the end cap. This one way drive mechanism in the described preferred embodiment comprises what may be referred to aptly, and be conveniently denominated as, a "screw type ramp and cliff means." It is one which is capable of axially moving an axially moveable member a predetermined axial distance in one direction only. This in turn determines the force required to move the cap member not by rotating the assembly but by applying the force axially to withdraw it and gain access to a drug load in a syringe. This invention provides structure for a predetermined tightness of the cap once installed on the nozzle of a mating syringe. Thus, the invention facilitates recycling of unused drugs. This one way drive mechanism is referred to and described where appropriate as a "ramp and cliff means" in this specification although other equivalent structure may be provided to achieve the same result in the same way within the spirit of the invention as is well known in this art.

An overall object is to provide an end cap assembly which, once installed on a syringe, will reveal if an axial force has been applied to separate it from the syringe that is greater than occurs in normal transport and handling and is great enough to break the sealed condition of a drug loaded in the syringe possibly compromising it so that it cannot be recycled with assurances of safety.

It is a general object to disclose the forms of the invention in a best mode and in preferred embodiments; and accordingly this disclosure is addressed to those in the art in sufficient detail to make and use the invention, which may be transported and stored in a sterile condition, is composed of readily available materials and structure which is easy to use, and is otherwise well adapted for the purposes expressly and implicitly indicated herein.

It is also an object of the invention to provide a process of making the invention in its various forms and of using it.

In accordance with these and other objects which will be apparent to those in the field, the subject invention is described in the following paragraphs on reference to the accompanying drawings illustrating the invention in a preferred embodiment which is not intended to be limiting.

BRIEF DESCRIPTION OF THE DRAWINGS

FIG. 1 is a general pictorial view representing one of many known standard syringes and which is representative of one on which the end cap assembly invention is to be installed for use in capping it after a drug has been loaded into it.

FIG. 2 is a side view, which has been partially broken away, of the luer lock syringe cap, generally having a male thread, either an end flange, as shown, or a set of circumferentially spaced ears, and which in assembly is captivated as a part within the subject end cap assembly.

FIG. 3 is a pictorial view illustrating only a part of the cap assembly, namely, a cup shaped end cap member.

FIG. 4 is a side view in cross section of the end cap member seen in FIG. 3.

FIG. 5 is a view in cross section of the end cap member seen in FIGS. 3 and 4 taken along line 5—5.

FIG. 6 is a detail view in partial cutaway of the end cap member shown in FIG. 5.

FIG. 7 is a cross sectional view along line 7—7 of FIG. 6.

FIG. 8 is a side view of an end wall or floor piece which closes one end of the end cap member of FIGS. 3, 4 and 5.

FIG. 9 is a left side view of FIG. 8 illustrating the configuration of the one way drive component and the centering means of this element.

FIG. 10 is an enlarged detailed view of the end wall or floor piece of FIG. 8.

FIG. 11 is view in cross section of the end cap assembly of the subject invention composed of the syringe cap seen in FIG. 2, the end cap member seen in FIGS. 3, 4 and 5, and the end wall member or floor piece seen in FIGS. 8 and 9.

FIG. 12 is an exploded view illustrating the relative arrangement of the elements prior to composing the end cap assembly seen in FIG. 11.

DETAILED DESCRIPTION OF THE PREFERRED EMBODIMENT

Figure 13:
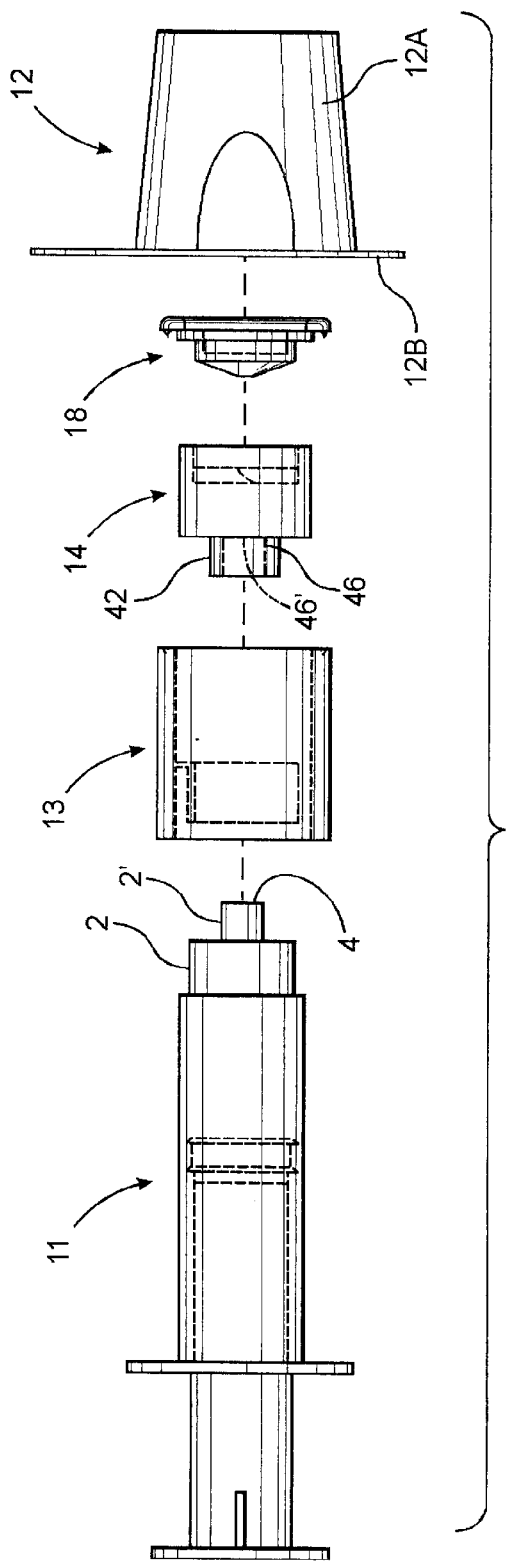
FIG. 13 is an enlarged exploded view illustrating the relative arrangement of the syringe, the end cap assembly parts, and the sterile package for the end cap parts after it is assembled, it being noted that the actual syringe cap is captivated within the end cap assembly when it is removed from the sterile package for a final assembly on a drug loaded syringe to sealingly close it.
Figure 14:
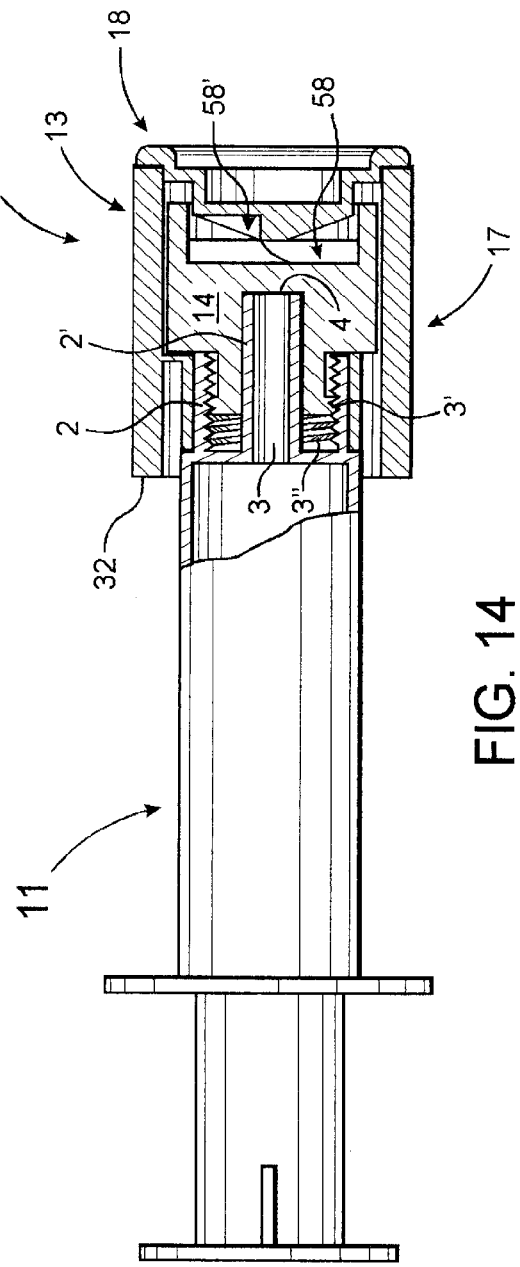
FIG. 14 is a side view in partial section and cutaway of the embodiment of FIG. 11 in assembled form.

Generally, FIG. 11 discloses the present invention in at least a partially assembled form 17. It is a tamper evident cap assembly 10 for a drug loaded syringe. The cap assembly 10 includes a specially shaped and captivated syringe cap 14 within it. In use, the syringe cap 14, is applied over the discharge port 4 on the end cannula 2' of the nozzle 2 of a conventional syringe 11, of the type shown in FIG. 1, after it has been loaded with a drug. This closes and seals, or caps, the opening or discharge port 4 of a lumen 3 which is formed within cannula 2' and is in fluid communication with the drug in the syringe barrel 1. A supply of end cap assemblies 10 each in an individual package 12 may be kept at a drug dispensing location, although a package may contain multiple end caps assemblies 10 if desired. Prior to use, each of the end cap assemblies 10 is in a sterile condition having been packaged, transported to, and stored at the drug dispensing location in a sterile packaged form for use, upon removal of it from the package, in capping a drug loaded syringe.

The invention in its basic form is an improved tamper evident syringe cap assembly 10.

Also, a form of the invention is the combination of the tamper evident end cap assembly 10, including the captivated luer lock cap within it, and a drug loaded standard syringe 11. When the end cap assembly 10 is installed on a mated drug loaded standard syringe 11, the end cap assembly 10 and syringe 11 cannot be disassembled in a tampering effort to "get at" the loaded drug without causing the end cap assembly 10 to break into pieces leaving "tell tale" evidence of the tampering. As will be discussed in greater detail hereinafter, at least one of the pieces is in the form of a tampering indicator ring 20 that floats free, after tampering, on the syringe nozzle 2.

Further, prior to assembly of the tamper evident end cap assembly 10 with a drug loaded syringe, the end cap assembly 10, while in an individual package 12, as it is generally disclosed herein, constitutes an end cap assembly and package combination disclosed in an unassembled relation in FIG. 12. When individually contained within package 12, the combination of FIGS. 11 and 12 is adapted for a) sterilization as a manufacturing step, b) storage with a substantial shelf life in a warehouse, c) shipment on demand to a drug dispensing facility, d) a second storage period at the facility, and e) subsequent use at the medical facility. By reason of the disclosed sterile structure of the combination 17, composed of the end cap assembly 10 and its package 12, the package 12 may be readily opened and the end cap assembly combination 17 of FIG. 11 removed from it and installed on a drug loaded syringe 11 for delivery to a patient to be ultimately used there by dosing a patient. In fact, the package 12 may be utilized to grip the end cap assembly while it is being installed so that the sterile condition of the end cap assembly 10 is not compromised by "hands on" manipulation of it. As shown in FIGS. 12 and 13, the package 12 may comprise a shell like body 12A disposable in surrounding and enclosing relation to the assembled end cap assembly combination 17 as disclosed in FIG. 11. A radially extending peripheral flange 12B may also be provided for purposes of handling and/or separation of the package 12 from the combined end cap assembly 10, as indicated as 17 in FIG. 11.

Structure of the Luer Lock Syringe Cap

Lure lock caps and like structures for syringe nozzles are not new in the art. The structure of a luer lock cap 14 of this invention is, however, different from known structures and is described conveniently on reference to FIG. 2. It includes a body 40 having a) a first axially extending portion 42 of a relatively small diameter with an end face 44 and a blind axially extending channel 46 with a closed inner end 46', and b) a second oppositely extending portion 48 of a larger diameter than that of the first portion 42 which has an opposite end face 50 and which also has a blind or closed axial recess 51 extending toward, but not to, the channel 46. The channel 46 receives nozzle 2, wherein end 46' restricts fluid from exiting discharge port 4. An annular skirt 52 defines an axially facing septum surface 54 within the skirt. On the first axially extending portion 42, a connection means 3' in the form of an annular flange, is provided for threaded attachment on a standard syringe nozzle portion 2 equipped with a mating thread means 3" to open or to close the syringe discharge port 4, as is conventional. Alternatively, lugs or a set of circumferentially spaced ears may be provided to threadably engage a companionate thread means portion in a skirt on the discharge end of a syringe nozzle portion 2. The interior septum surface 54 of the syringe end cap 14, located within the skirt 52 is formed with a pattern in relief. The pattern results in a pair of diametrically spaced ramp and cliff means, comprising a first one way drive structure 58 disposed and structured to engage a mating surface constituting a second drive structure 58' formed the floor piece 18 as shown in FIGS. 8 and 9, which is described hereinafter. Medical grade materials for the luer cap are well known, conventionally used in the art, readily available, and suitable for the luer lock syringe cap 14 as well as the other parts of the invention.

General overview of the Structure of Tamper Evident Cap Assembly

The tamper evident end cap assembly 10 is composed of two chief structural elements: a generally cup or sleeve shaped end cap member 13 which forms a shield, and the syringe cap 14 loosely captivated within the end cap member 13. Importantly, the end cap member 13 further includes an end wall piece or floor piece 18 comprising means to captivate the syringe cap 14 within the end cap member 13, constraining it such that generally only a rotational and limited axial movement occurs between the septum surface 54 and the end wall or floor piece 18. Simply put, the syringe cap 14 is free to rotate in the end cap member 13 but it is captivated loosely, as opposed to tightly within the end cap member 13; and it is constrained to only limited axial movement of a predetermined distance in one axial direction only. To this purpose, the inner end face of the floor piece 18 is configured to form a pattern in relief comprising the aforementioned second, one way drive structure 58', which is sized and configured to mate with the first mentioned pattern in relief comprising the first drive structure 58 and which is a mirror image of the pattern in relief of the first drive structure 58 formed on the septum face 54 in the syringe cap 14. These components engage one another upon assembly and comprise a one way drive assembly 58 and 58' for installing the combined assembly 17 of FIG. 11 on a syringe nozzle 2. In other words the floor piece 18, specifically its inner end surface when disposed in the cup shaped member 13, and the captivated syringe cap 14, specifically its septum surface 54 within the skirt 52, confront one another, engage and comprise a one way drive assembly 58 and 58' to axially displace the syringe a predetermined axial distance on relative rotation of these two pieces for installing of the end cap assembly 10, as a whole, on a drug loaded syringe. This one way drive assembly to engage and drive the confronting first and second drive structures 58 and 58' are seen best indicated in the assembled combination 17 including the end cap assembly 10 of FIG. 11.

Structure of the Cup Shaped End Cap Member or Sleeve Form Shield Element

The end cap member 13 is best seen in FIGS. 3 through 5. It comprises: a) an outer tubular sleeve 16; b) a cup floor piece 18 or end wall (see FIGS. 8 and 9); c) an inner tubular sleeve 20 or indicator ring; and c) a connecting assembly including one or more frangible tabs or chads 22, normally connecting the outer sleeve 16 and indicator ring 20 together in co-axial relation. In at least one preferred embodiment, a centering means 24 on surface 57' of the floor piece 18, together with the recess 34, serves the purpose of centering the floor piece 18 on the end cap member 13. The centering means 24 may comprise an outwardly extending rib or rib segment disposed to be received within one or more correspondingly dimensioned grooves or recesses 34 formed in end face 28 of end cap member 13, as best shown in FIGS. 10 and 4 respectively.

Referring to the floor piece 18, as disclosed in FIGS. 8–10 and 12, it is of the preferred shape and size relative to the end cap 13 as shown. It is seen that it is of a generally circular plate configuration and has a first or outer main axially facing surface 51 and a second or inner main axially facing surface 53. The inner or second main face 53 is echelon in shape as seen from the side; and the outside surface 51 may be flat or, as shown, axially recessed, see FIG. 8. This forms an outer support surface 55. A central raised circular surface 57 extends into the cup shaped end cap member 13, an outermost circular surface 57' engages the end face 28 of end cap 13, and a circular surface 59 of a radial dimension adequate to loosely engage the open end face of the syringe cap 14 inside the skirt 52 permitting non-binding rotation of the floor piece 18 and the cup shaped end cap member 13 relative to the syringe cap 14. The distal tip of the raised circular surface 59 is preferably cone shaped to provide centering action to guide seating of the syringe cap 14 within the cup shaped end cap member 13 during manufacture of the end cap assembly 10. The surface 53 is also configured to form diametrically spaced ramp and cliff means defining the second drive structure 58' to cooperate with a pair of diametrical ramp and cliff means defining the first drive structure 58 on the syringe cap 14. These constitute, when engaged and mated [a] the aforementioned one way drive assembly to advance the syringe cap 14 when being installed on a syringe 11. In a sense the end wall or floor piece 18 constitutes a tool or means to position and to secure the syringe cap 14 to a correct degree of tightness on the syringe nozzle 2 at a predetermined axial location on the nozzle 2 of a mating standard syringe 11. The floor piece 18 also comprises a generally disk shaped blocking means to keep the syringe cap in assembly so it cannot fall out. It also is of sufficient structure to support the end cap 13 when assembled with the syringe cap 14 within in it. In a preferred embodiment not shown the entire outer surface 51 of the floor piece 18 may be flat rather than recessed as shown.

The end cap member 13 has a bore or space 26 of a first predetermined diameter defining an open axially facing mouth 28 and, axially spaced therefrom, an opposite annular axially facing surface 32. In a preferred embodiment, the axial length is 0.805 inch; the outside diameter is 0.680; the inside diameter is 0.488.

The ring indicator ring 20 is coaxially located within the receptacle or bore 26; and it has an outer cylindrical surface 36 and opposite annular axial first and second faces, 38 and 40. It is of an axial length of 0.250; also it is of an outside diameter of 0.488 and an inside diameter of 0.385; and its first axial face 38 is recessed 0.490 from the axially facing mouth 28.

A breakable connecting assembly disposed between the outer sleeve 16 of end cap member 13 and the inwardly disposed indicator ring 20 comprises a plurality of circumferentially spaced, frangible lugs, cads or tabs 22. More specifically from the out side ring surface 36 at equiangularly spaced locations of two, three or more, the radially extending lugs 22, extend radially outward. The lugs 22 connect the indicator ring 20 to the outer sleeve 16 maintaining it in the illustrated recessed location in the outer sleeve 16. The lugs 22 are of a common maximum cross section of 0.045 in a circumferential measurement and have a semicircular cross section, as best shown in FIG. 7, of a radius of curvature of less dimension than its circumferential dimension so that the lugs 22 are weakened and are easily breakable in response to axial forces tending to separate the indicator ring 20 from the outer sleeve 16 of the end cap member 13.

The end cap member 13 as described, absent the end wall or floor piece 18 , as will be appreciated by those skilled in the art, may be of a one piece molded material, as is the floor piece 18.

Assembly of the End Cap and Captivated Syringe Cap

With the end wall or floor piece 18 not assembled to close the end opening 28 in the outer sleeve 16, the syringe cap 14 is moved axially into the outer sleeve 16 with the reduced diameter portion 42 being received within the inner sleeve or indicator ring 20 and advanced until the shoulder 42' of the syringe cap 14 abuts the end 38 of the indicator ring 20. As such, the syringe cap 14 is loosely positioned within the end cap 13. Then the end wall or floor 18 is fixedly connected to the end cap member 13 as shown in FIG. 11 by suitable well known means, such as by ultrasonic welding, closing the open end 28 and trapping the syringe cap 14 and captivating it loosely. This assembled combination 17 of FIG. 11 is thus made ready for gassing after positioning it in a closed package to sterilize it.

Assembly of the End Cap Assembly on a Loaded Syringe Nozzle

At a pharmacy station of a facility, a standard syringe 11 for that particular facility is loaded with a drug. Thereafter, the end cap assembly 10 is removed from the package 12 which is of plyable material preferably in the case of an individually packaged end cap assembly; and it is then advanced onto the syringe nozzle 2 by threadably advancing the syringe cap 14 into a tightened position on the syringe nozzle 2 at a predetermined axial distance from the drug discharge port 4, closing it and enshrouding the adjacent surface of the nozzle 2. It is to be noted that this may be done without comprising the sterility of the end cap assembly 10. The end cap member 13 serves as a tool for advancing the syringe cap 14 upon tightening rotation of it through the one way drive comprising the mating formed surfaces 58 and 58' of the syringe cap 14 and the end cap floor piece 18 respectfully. This does not require touching the nozzle 2 or the syringe cap 14. Upon an attempt to reverse the direction of rotation of the end cap member 13 from the nozzle 2, the first and second drive structures 58 and 58' respectively, disconnect from one another, allowing relative movement between the floor piece 18 and the syringe cap 14. Therefore, rotation of the end cap member 13 in the "wrong" direction cannot be used to remove the tamper proof end cap 13 from the syringe nozzle 2. Thereafter, access is impossible to the drug in the syringe with the exception of an outward axial force being applied to the end cap member 13 of sufficient magnitude to break the indicator ring 20 free from the outer end cap sleeve 16. This, of course is only done by one authorized to dose a patient or to recycle an unused drug charge. However, if done by an unauthorized person, such as a delivery person while making rounds delivering the loaded syringe to a nurse station, the tampering would be immediately apparent because the indicator ring 20 would either be gone or loosely trapped on the syringe nozzle 2 between the syringe barrel 1 and syringe cap 14. In short, if tampering were to take place, the fact that the indicator ring 20 had been broken free from the outer sleeve 16 would be indicated either by its absence or it being loosely trapped on the syringe nozzle 2 between the shoulder at the juncture of the syringe barrel 1 and the nozzle 2. If, then, the syringe cap 14 were to be threadably withdrawn to gain access to the drug and something else substituted for it in an effort to disguise what had happened, this also would be evident because the end cap member 13 on the syringe 11 would be loose and wobble on the syringe cap 14. In summary if an unauthorized action of tampering were to take place or an unauthorized removal of the luer lock syringe cap 14 were to occur, it would alert others to that having happened.

The Sterile Package Including an End Cap Assembly

The end cap assembly 10 may be color coded, for example red may indicate morphine and a different color might indicate a different drug. An end cap assembly 10 according to the invention may be packaged in a non porous plastic tray or blister pack with an out turned open lip surface formed about an open mouth, which is spanned by a lid composed of sheet material which is peelable. The material of the lid is preferably Tyvek, a sterile packaging of spunbonded olefin manufactured from very fine filaments of high-density polyethylene bonded together by heat and pressure. Tyvek is the trademark of the material; and it is made by the E.I. DuPont Company of Wilmington, Del. or one of its subsidiaries. It permits sterilization by a gas under pressure and release of the gas; but it prohibits passage of micro organisms into the package and therefore maintains the end cap assembly in the tray in a sterile condition prior to use. An individual assembly is preferred in each tray or blister with a separate lid associated with each tray or pack. This is because the sterility of all of a plurality of end cap assemblies in the same tray or package may become contaminated and compromised when the a tray lid is removed exposing all within the tray to ambient conditions. In a preferred embodiment the assemblies may be in a row of trays joined together in a strip with cross perforations so that individual packets may be severed from the strip. Preferably the lids are provided with a tab to initiate peeling to expose an assembly, especially when only one of a particular color code is required at a time.

In general it will be appreciated that the dimensions of the standard syringe will dictate important dimensions of the luer lock syringe cap 14. For example, the diameter dimension of the recess in the luer lock syringe cap 14, which, in assembly, receives the distal end or nozzle 2 of the syringe 11, and the dimensions of the mating thread means on the outside diameter as at 3' of the luer lock syringe cap 14, are dictated by the dimensions of the particular standard syringe 11 which is outfitted with the invention. Similarly the outside diameter of the enlarged portion 48 of the luer lock syringe cap 14 will establish the permissible range of the diameter of the interior sleeve or indicator ring 20; and so forth, with regard to the dimensions of each of the elements of the end cap assembly 10. Hence, the actual dimensions set forth herein constitute no significant part of the invention in and of themselves and, rather, it is the relative dimensions of the elements disclosed which is significant and the selection of which is well within the ordinary skill of those in the art to which this subject matter is useful and who wish to practice the invention.

Accordingly the dimensions referred to herein are not intended to be limiting and are illustrative only.

While the disclosure of this invention has been shown and described in a preferred embodiment and in a best mode, it is recognized that departures therefrom may be within the spirit and scope of the invention which is therefore not to be limited except by the claims and within the doctrine of equivalents.

Now that the invention has been described,

What is claimed is:

1. A tamper evident end cap assembly for a syringe having a nozzle with a discharge port, said assembly comprising:
   a) an end cap member including at least one open end dimensioned to receive the nozzle therethrough,
   b) an indicator ring disposed within said end cap member and a connecting assembly releasably securing said indicator ring to said end cap member,
   c) said connecting assembly structured to disconnect said indicator ring from said end cap member upon a predetermined force being applied to said end cap member,
   d) a syringe cap movably disposed within said end cap member and axially positionable into a fluid restricting position relative to the discharge port, and
   e) a drive assembly partially mounted on said end cap member and structured to rotate said syringe cap in only a single direction for disposition of said syringe cap in said fluid restricting position.

2. An end cap assembly as recited in claim 1 wherein said indicator ring is disposed in surrounding relation to at least a portion of the nozzle and between said syringe cap and said one open end of said end cap member.

3. An end cap assembly as recited in claim 2 wherein said connecting assembly comprises a frangible structure interconnected between said end cap member and said indicator ring.

4. An end cap assembly as recited in claim 3 wherein said predetermined force comprises an axial force of sufficient magnitude to remove said end cap member from the nozzle, said syringe cap and said indicator ring.

5. An end cap assembly as recited in claim 3 wherein said frangible structure comprises a plurality of spaced apart tabs disposed in interconnecting relation between an outer surface of said indicator ring and an inner surface of said end cap member.

6. An end cap assembly as recited in claim 1 wherein said drive assembly is secured to both said end cap member and said syringe cap and structured for axial disposition of said syringe cap into said fluid restricting position upon rotation of said end cap member in only one of two opposite directions.

7. An end cap assembly as recited in claim 1 wherein said drive assembly comprises a first drive structure mounted on said syringe cap and a second drive structure mounted on said end cap member.

8. An end cap assembly as recited in claim 7 wherein said first and second drive structures are relatively disposed and cooperatively structured to axially position said syringe cap into said fluid restricting position upon rotation of said end cap member in only a first direction.

9. An end cap assembly as recited in claim 8 wherein each of said first and second drive structures comprise a ramp and cliff assembly disposed and structured for mating engagement with one another.

10. An end cap assembly as recited in claim 9 wherein said ramp and cliff assemblies are disposed to rotate relative to one another in a second, opposite direction.

11. An end cap assembly as recited in claim 10 wherein said first drive structure is mounted on said syringe cap, said second drive structure is mounted on a floor piece secured to one end of said end cap member.

12. A tamper evident end cap assembly for a syringe having a nozzle with a discharge port, said assembly comprising:
   a) an end cap member including an at least one open end dimensioned to receive the nozzle therethrough,
   b) an indicator ring disposed within said end cap member and a connecting assembly releasably securing said indicator ring to said end cap member,
   c) said connecting assembly structured to disconnect said indicator ring from said end cap member upon a predetermined force being applied to said end cap member,
   d) a syringe cap movably disposed within said end cap member and axially positionable into a fluid restricting position relative to the discharge port,
   e) a drive assembly comprising a first drive structure mounted on said syringe cap and a second drive structure mounted on said end cap member, and
   f) said first and second drive structures being disposed in confronting relation to one another and being cooperatively structured to axially position said syringe cap into said fluid restricting position upon rotation of said end cap member in only a single direction.

13. An end cap assembly as recited in claim 12 wherein each of said first and second drive structures comprise a ramp and cliff assembly disposed and structured for mating engagement with one another.

14. An end cap assembly as recited in claim 13 wherein said ramp and cliff assemblies are disposed to rotate relative to one another in a first direction and rotate with one another in a second direction.

15. An end cap assembly as recited in claim 12 further comprising a floor piece secured to said end cap member in substantially opposing relation to said open end.

16. An end cap assembly as recited in claim 15 wherein said first drive structure is mounted on said syringe cap and said second drive structure is mounted on an inner surface of said floor piece in confronting relation to said first drive structure.

* * * * *